US009717463B2

United States Patent
Hayashi et al.

(10) Patent No.: US 9,717,463 B2
(45) Date of Patent: Aug. 1, 2017

(54) BIOLOGICAL INFORMATION MEASUREMENT METHOD AND APPARATUS WITH VARIABLE CUTOFF FREQUENCY LOW PASS FILTER (71) Applicant: Murata Manufacturing Co., Ltd., Nagaokakyo-shi, Kyoto-fu (JP)

(72) Inventors: Takanori Hayashi, Kyoto (JP); Yasushi Sato, Kyoto (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 15/078,139

(22) Filed: Mar. 23, 2016

(65) Prior Publication Data
US 2016/0199006 A1 Jul. 14, 2016

Related U.S. Application Data (63) Continuation of application No. PCT/JP2014/074373, filed on Sep. 16, 2014.

(30) Foreign Application Priority Data

Sep. 26, 2013 (JP) ................................. 2013-199795

(51) Int. Cl.
*A61B 5/0428* (2006.01)
*A61B 5/00* (2006.01)
(Continued)

(52) U.S. Cl.
CPC ............ *A61B 5/721* (2013.01); *A61B 5/0245* (2013.01); *A61B 5/02416* (2013.01);
(Continued)

(58) Field of Classification Search
None
See application file for complete search history.

(56) References Cited

U.S. PATENT DOCUMENTS 3,495,596 A * 2/1970 Condict ............... A61B 5/0476
607/62
RE31,097 E * 12/1982 Vas .......................... A61B 5/11
600/500
(Continued)

FOREIGN PATENT DOCUMENTS

JP       5-90842 A      4/1993
JP    10-248819 A      9/1998
(Continued)

OTHER PUBLICATIONS

International Search Report for PCT/JP2014/074373, date of mailing Dec. 22, 2014.

(Continued)

*Primary Examiner* — Kennedy Schaetzle
(74) *Attorney, Agent, or Firm* — Arent Fox LLP (57) ABSTRACT

A biological information measurement apparatus includes a phase/frequency comparison unit that outputs a deviation signal based on a phase difference between a biological signal and an oscillation signal; a loop filter; and a voltage controlled oscillation unit that generates the oscillation signal in accordance with the deviation signal that has passed through the loop filter. The apparatus further includes a CPU that estimates a SN ratio of the biological signal and analyzes a phase difference/frequency difference between the biological signal and the oscillation signal. A variable low pass filter is provided that selectively blocks a signal of a predetermined frequency band contained in the deviation signal that has passed through the loop filter and the CPU changes a cutoff frequency of the variable low pass filter based on the SN ratio and the phase difference/frequency difference.

20 Claims, 5 Drawing Sheets (51) Int. Cl.
   *A61B 5/024*    (2006.01)
   *A61B 5/0245*   (2006.01)
   *H03L 7/08*     (2006.01)
   *A61B 5/0452*   (2006.01)
   *A61B 5/0456*   (2006.01)

(52) U.S. Cl.
   CPC .......... *A61B 5/02427* (2013.01); *A61B 5/725* (2013.01); *A61B 5/7207* (2013.01); *A61B 5/7225* (2013.01); *A61B 5/7246* (2013.01); *A61B 5/7253* (2013.01); *H03L 7/0805* (2013.01); *A61B 5/0452* (2013.01); *A61B 5/0456* (2013.01)

(56) References Cited

U.S. PATENT DOCUMENTS

| | | | | |
|---|---|---|---|---|
| 7,385,443 | B1* | 6/2008 | Denison | H03F 3/38 330/10 |
| 9,351,653 | B1* | 5/2016 | Harrison | A61B 5/04014 |
| 2006/0173364 | A1* | 8/2006 | Clancy | A61B 5/04 600/485 |
| 2009/0046295 | A1* | 2/2009 | Kemp | A61B 5/0066 356/479 |
| 2011/0227571 | A1 | 9/2011 | Sekiguchi et al. | |

FOREIGN PATENT DOCUMENTS

| | | |
|---|---|---|
| JP | 10-285021 A | 10/1998 |
| JP | 2003028952 A | 1/2003 |
| JP | 2007105133 A | 4/2007 |
| JP | 2007251571 A | 9/2007 |
| JP | 2011189079 A | 9/2011 |

OTHER PUBLICATIONS

Written Opinion for PCT/JP2014/074373, date of mailing Dec. 22, 2014.

* cited by examiner

BIOLOGICAL INFORMATION MEASUREMENT METHOD AND APPARATUS WITH VARIABLE CUTOFF FREQUENCY LOW PASS FILTER

CROSS REFERENCE TO RELATED APPLICATIONS

The present application is a continuation of PCT/JP2014/074373 filed Sep. 16, 2014, which claims priority to Japanese Patent Application No. 2013-199795, filed Sep. 26, 2013, the entire contents of each of which are incorporated herein by reference.

FIELD OF THE INVENTION

The present invention relates to biological information measurement apparatuses, and particularly relates to biological information measurement apparatuses that have phase synchronization circuits.

BACKGROUND OF THE INVENTION

Phase synchronization circuits that output an oscillation signal whose phase is synchronized with an input signal (also called "PLLs", or "phase locked loops", hereinafter) have for some time been widely used in applications such as suppressing jitter in input signals of communication apparatuses and the like, clock frequency crossover, and so on. Phase synchronization circuits are also applied in apparatuses that measure biological information, such as heart rate, pulse rate, or the like (see Patent Document 1, for example). A light-receiving device described in Patent Document 1 converts a pulse wave signal contained in an optical signal detected by a light-receiving element into a digital signal using a hysteresis comparator, and measures a pulse beat interval by measuring an interval of pulses in the digital signal with a timer that uses a phase synchronization circuit.

Patent Document 2, meanwhile, discloses a phase synchronization circuit that, in consideration of jitter and the like in an input signal, changes a cutoff frequency of a loop filter so as to stabilize the output of an oscillation signal. Specifically, in addition to a first phase synchronization circuit including a first phase comparator, a first loop filter, and a first oscillation circuit, this phase synchronization circuit further includes a PLL circuit that generates a reference signal whose phase is synchronized with the input signal and that has less phase noise than the input signal, a second phase comparator that detects a phase difference between the input signal and the reference signal, a low pass filter that integrates that output, and a filter control unit that controls the cutoff frequency of the first loop filter based on a frequency component obtained by analyzing the frequency of that output. The cutoff frequency of the first loop filter is changed in accordance with jitter in the input signal.

Patent Document 1: Japanese Unexamined Patent Application Publication No. 2007-105133.

Patent Document 2: Japanese Unexamined Patent Application Publication No. 2007-251571.

Incidentally, because pulse rates vary over time, biological signals such as electrocardiographs, photoplethysmographs, and so on experience a wider range of frequency fluctuation than the jitter in an input signal of a communication apparatus or the like, and are also more susceptible to artifacts (noise) superimposed on the signal due to body movements or the like.

Here, in the case where the phase synchronization circuit disclosed in Patent Document 2 is applied in an apparatus that measures biological information, an output signal that is less affected by jitter can be obtained by comparing the phases of the output of the PLL circuit, which has little phase noise, with the input signal (biological signal) in order to extract only a jitter component, and then controlling the cutoff frequency of the loop filter in accordance with the amount of jitter. However, according to this phase synchronization circuit, fluctuations in the output of the phase comparator caused by fluctuations in the base frequency of the biological signal cannot be distinguished from fluctuations in the output of the phase comparator caused by artifacts such as jitter. Therefore, even if there is no jitter in the biological signal, when the base frequency of the biological signal fluctuates suddenly, the cutoff frequency of the loop filter is controlled in the same manner as if there was superimposed jitter, which can greatly worsen the lock-up time of the PLL.

SUMMARY OF THE INVENTION

It is an object of the present invention to provide, in a biological information measurement apparatus having a phase synchronization circuit, a biological information measurement apparatus capable of handling fluctuations in a base frequency of a biological signal and obtaining an output signal (frequency synchronization signal) in which artifacts are suppressed.

A biological information measurement apparatus according to the present invention includes a biological signal detecting unit or sensor that detects a biological signal; a phase/frequency comparator that outputs a deviation signal based on a phase difference/frequency difference between the biological signal detected by the biological signal detecting unit and an oscillation signal; a loop filter unit that selectively blocks a signal in a predetermined frequency band contained in the deviation signal outputted by the phase/frequency comparator; a voltage controlled oscillator that generates and outputs an oscillation signal in accordance with the deviation signal that has passed through the loop filter unit; a biological signal analyzing unit that analyzes a phase, a frequency, and a SN ratio of the biological signal; a variable low pass filter unit capable of changing a cutoff frequency and that selectively blocks a signal of a predetermined frequency band contained in the deviation signal that has passed through the loop filter unit; and a parameter control unit that changes the cutoff frequency of the variable low pass filter unit based on an analysis result obtained by the biological signal analyzing unit.

According to the biological information measurement apparatus of the present invention, the phase, frequency, and SN ratio of the biological signal are analyzed, and the cutoff frequency of the variable low pass filter unit is changed in accordance with that analysis result. Accordingly, the cutoff frequency of the variable low pass filter unit can be adjusted dynamically in accordance with fluctuations in the frequency of the inputted biological signal, the state of artifacts, and so on. As such, a biological information measurement apparatus having a phase synchronization circuit comprised of a phase/frequency comparator, a loop filter unit, and a voltage controlled oscillator can obtain an output signal (a frequency synchronization signal) capable of responding to fluctuations in the base frequency of the biological signal and in which artifacts are suppressed.

In the biological information measurement apparatus according to the present invention, it is preferable that the biological signal analyzing unit analyze the phase, the frequency, and the SN ratio of the biological signal by carrying out an orthogonal transform on the biological signal.

According to this configuration, the phase, frequency, and SN ratio of the biological signal, in which the pulse rate varies over time and which is easily susceptible to superimposed artifacts caused by body movements and the like, can be analyzed appropriately.

In the biological information measurement apparatus according to the present invention, it is preferable that the biological signal analyzing unit include an SN analyzing unit that estimates the SN ratio of the biological signal by carrying out an autocorrelation analysis on the biological signal and a phase/frequency analyzing unit that analyzes the phase difference/frequency difference between the biological signal and the oscillation signal based on the output of the phase/frequency comparator, and that the parameter control unit change the cutoff frequency of the variable low pass filter unit based on the the SN ratio estimated by the SN analyzing unit and the phase difference/frequency difference analyzed by the phase/frequency analyzing unit.

In this case, the cutoff frequency of the variable low pass filter unit is dynamically changed in accordance with the analysis result from the SN analyzing unit (the SN ratio) and the analysis result from the phase/frequency analyzing unit (the phase difference/frequency difference). Accordingly, the cutoff frequency can be adjusted more appropriately in accordance with fluctuations in the frequency of the inputted biological signal, the state of artifacts, and so on. As such, an output signal (frequency synchronization signal) capable of responding to fluctuations in the base frequency of the biological signal and in which artifacts are suppressed can be obtained.

In the biological information measurement apparatus according to the present invention, it is preferable that the parameter control unit reduce the cutoff frequency of the variable low pass filter unit more in the case where the SN ratio is lower than a predetermined value than in the case where the SN ratio is greater than or equal to the predetermined value.

According to this configuration, the cutoff frequency of the variable low pass filter unit is further reduced in the case where the SN ratio of the biological signal is lower than a predetermined value, or in other words, in the case where artifacts are superimposed on the biological signal. Accordingly, a frequency synchronization signal in which the influence of artifacts is appropriately suppressed can be obtained.

In the biological information measurement apparatus according to the present invention, it is preferable that the parameter control unit reduce the cutoff frequency of the variable low pass filter unit more as the SN ratio decreases.

According to this configuration, the cutoff frequency of the variable low pass filter unit is reduced as the SN ratio decreases, or in other words, as more artifacts are superimposed on the signal. Accordingly, the cutoff frequency can be adjusted more appropriately in response to the extent of the artifacts.

In the biological information measurement apparatus according to the present invention, it is preferable that the parameter control unit increase the cutoff frequency of the variable low pass filter unit more in the case where the SN ratio is greater than or equal to the predetermined value and the phase difference/frequency difference is greater than or equal to the predetermined threshold value than in the case where the SN ratio is lower than the predetermined value and/or the case where the phase difference/frequency difference is lower than the predetermined threshold value.

According to this configuration, the cutoff frequency of the variable low pass filter unit is increased in the case where the SN ratio is greater than or equal to the predetermined value and the phase difference/frequency difference is greater than or equal to the predetermined threshold value, or in other words, in the case where artifacts are not superimposed but a PLL is not synchronized. Accordingly, the tracking properties with respect to fluctuations in the base frequency can be improved.

It is preferable that the biological information measurement apparatus according to the present invention further include a delay unit, provided between the loop filter unit and the variable low pass filter unit, that delays the deviation signal that has passed through the loop filter unit and outputs the delayed signal to the variable low pass filter unit in accordance with an analysis time required by the SN analyzing unit and the phase/frequency analyzing unit.

According to this configuration, the time required for the analysis performed by the SN analyzing unit and the phase/frequency analyzing unit (that is, a delay time) can be compensated for appropriately.

According to the present invention, in a biological information measurement apparatus having a phase synchronization circuit, an output signal (frequency synchronization signal) capable of responding to fluctuations in the base frequency of the biological signal and in which artifacts are suppressed can be obtained.

DETAILED DESCRIPTION

Hereinafter, preferred embodiments of the present invention will be described in detail with reference to the drawings. In the drawings, the same reference numerals are used for identical or corresponding portions. Furthermore, in each of the drawings, the same reference numerals are appended to identical elements and redundant descriptions thereof will be omitted.

First Embodiment

Figure 1:
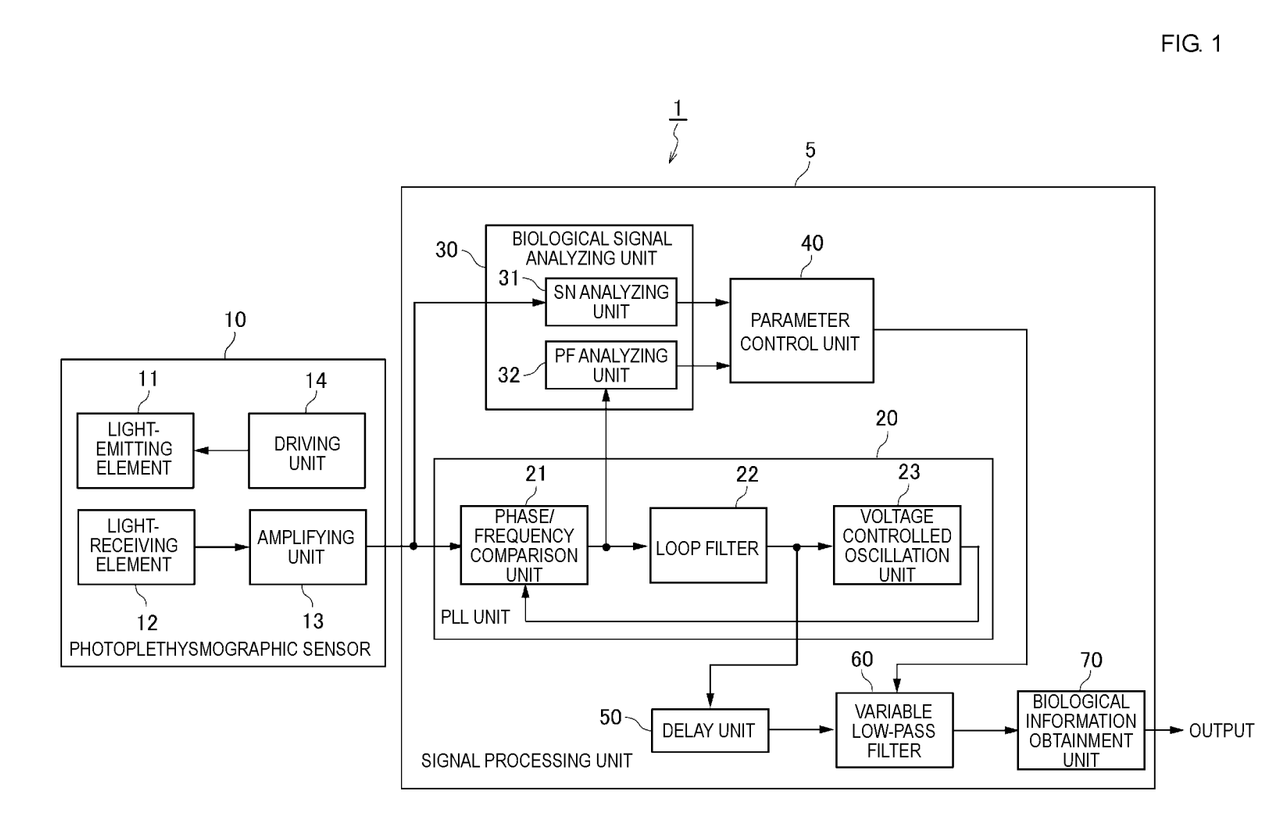
FIG. 1 is a block diagram illustrating the configuration of a biological information measurement apparatus according to a first embodiment.
Figure 2:
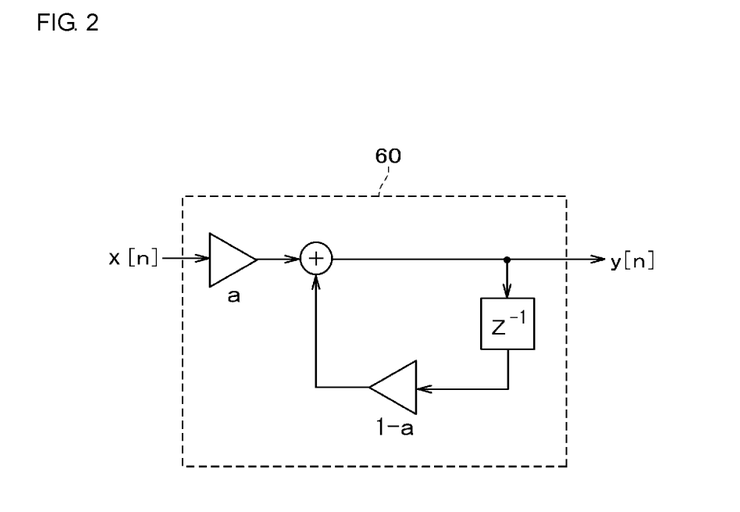
FIG. 2 is a diagram illustrating an example of a variable low pass filter included in the biological information measurement apparatus according to the first embodiment.

First, the configuration of a biological information measurement apparatus 1 according to a first embodiment will be described using FIGS. 1 and 2. FIG. 1 is a block diagram illustrating the configuration of the biological information measurement apparatus 1. FIG. 2 is a diagram illustrating an example of a variable low pass filter 60 included in the biological information measurement apparatus 1. The present embodiment describes, as an example, a case where biological information such as a pulse rate is measured from a photoplethysmographic signal that serves as a biological signal. However, the biological signal is not limited to a photoplethysmographic signal, and an electrocardiac signal or the like may be employed instead, for example.

The biological information measurement apparatus 1 detects a photoplethysmographic signal and generates a signal whose frequency is synchronized with the detected photoplethysmographic signal. Then, based on the generated signal, the biological information measurement apparatus 1 measures biological information such as a pulse rate (a base frequency of the photoplethysmographic signal). To that end, the biological information measurement apparatus 1 includes a photoplethysmographic sensor 10 that generates the photoplethysmographic signal, and a signal processing unit 5 that generates a signal whose frequency is synchronized with the photoplethysmographic signal and measures the biological information such as a pulse rate or the like. Various constituent elements will be described in detail hereinafter.

The photoplethysmographic sensor 10 is a sensor that uses light absorbance characteristics of bloodstream hemoglobin to optically detect the photoplethysmographic signal. The photoplethysmographic sensor 10 includes a light-emitting element 11, a light-receiving element 12, an amplifying unit 13, and a driving unit 14.

The light-emitting element 11 emits light in accordance with a pulse-form driving signal generated and outputted by the driving unit 14. For example, an LED, a VCSEL (Vertical Cavity Surface Emitting LASER), a resonant-type LED, or the like can be used as the light-emitting element 11.

The light-receiving element 12 outputs a detection signal based on the intensity of incident light that has been emitted from the light-emitting element 11 and then passed through a human body such as a fingertip or reflected by the human body. For example, a photodiode, a phototransistor, or the like can be effectively used as the light-receiving element 12. Note that a photodiode is used as the light-receiving element 12 in the present embodiment. The light-receiving element 12 is connected to the amplifying unit 13, and the detection signal (photoplethysmographic signal) obtained by the light-receiving element 12 is outputted to the amplifying unit 13.

The amplifying unit 13 is comprised of an amplifier using an op-amp or the like, for example, and amplifies the photoplethysmographic signal detected by the light-receiving element 12. The photoplethysmographic sensor 10 is connected to the signal processing unit 5, and the detected photoplethysmographic signal is outputted to the signal processing unit 5.

The signal processing unit 5 generates a signal whose frequency is synchronized with the photoplethysmographic signal detected by the photoplethysmographic sensor 10, and measures biological information such as a pulse rate (a base frequency of the biological signal). To that end, the signal processing unit 5 includes a PLL unit 20, a biological signal analyzing unit 30, a parameter control unit 40, a delay unit 50, the variable low pass filter 60, and a biological information obtainment unit 70. The PLL unit 20, meanwhile, includes a phase/frequency comparison unit (PFC) 21, a loop filter 22, and a voltage controlled oscillation unit (VCO) 23.

According to the exemplary embodiment, of the above-described units, the biological signal analyzing unit 30 (an SN analyzing unit 31 and a PF analyzing unit 32), the parameter control unit 40, the loop filter 22 (when comprised by a digital filter), the delay unit 50, the variable low pass filter 60, and the biological information obtainment unit 70 can be functional units or modules that are configured of a computer processing unit ("CPU") (or MCU) that carries out computational processes, a ROM that stores programs, data, and so on for causing that CPU to execute various processes, a RAM that temporarily stores various types of data such as processing results, and the like. In other words, the functions of the various above-described elements are realized by programs stored in the ROM being executed by the CPU. The present disclosure refers to each specific unit performing its associated algorithm, but it should be appreciated that such algorithms can be performed by the CPU according to the exemplary embodiment.

The PLL unit 20 compares the photoplethysmographic signal (an input signal) with an oscillation signal of the voltage controlled oscillation unit 23 (an output signal) using a phase/frequency comparison unit 21, and outputs a signal (a deviation signal) based on the magnitudes of a phase difference and a frequency difference. The deviation signal is then integrated using the loop filter 22 and inputted into the voltage controlled oscillation unit 23, thus generating (oscillating) the oscillation signal so as to eliminate the phase difference and the frequency difference between the oscillation signal of the voltage controlled oscillation unit 23 and the photoplethysmographic signal. The PLL unit 20 outputs a signal synchronized with the photoplethysmographic signal as a result of this series of operations.

As described above, the phase/frequency comparison unit 21 (i.e., a phase/frequency comparator) outputs a deviation signal based on the phase difference and the frequency difference between the obtained photoplethysmographic signal and the oscillation signal (a feedback signal) generated and outputted by the voltage controlled oscillation unit 23. To be more specific, when the difference between the photoplethysmographic signal and the oscillation signal is within one period, the phase/frequency comparison unit 21 compares the phases and outputs, as the deviation signal, a square wave of a positive or negative voltage with a duty ratio proportional to the phase difference. Meanwhile, when the difference between the photoplethysmographic signal and the oscillation signal exceeds one period, the phase/frequency comparison unit 21 functions as a frequency comparator, and outputs, as the deviation signal, a square wave of a positive or negative voltage with a duty ratio proportional to the frequency difference.

Note that a digital phase/frequency comparator, a voltage output phase/frequency comparator including a charge pumping circuit, or the like, for example, can be used as the phase/frequency comparison unit 21. The phase/frequency comparison unit 21 is connected to the loop filter 22 and the biological signal analyzing unit 30 (the PF analyzing unit 32), and the deviation signal indicating the phase difference and frequency difference between the photoplethysmographic signal and the oscillation signal is outputted to the loop filter 22 and the biological signal analyzing unit 30 (the PF analyzing unit 32).

The loop filter 22 is a low pass filter that selectively blocks only a signal in a predetermined frequency band contained in the deviation signal outputted by the phase/frequency comparison unit 21. By blocking unnecessary short-period fluctuations, the loop filter 22 suppresses needless oscillations that can arise due to short-period signal fluctuations being amplified in a circuit containing feedback.

An analog filter employing an operational amplifier (op-amp), for example, can be used as the loop filter 22. Meanwhile, a second-order IIR (infinite impulse response) filter (a digital filter) or the like, for example, may be used as the loop filter 22. The loop filter 22 is connected to the voltage controlled oscillation unit 23 and the delay unit 50, and an output signal (output voltage) from the loop filter 22 is outputted to the voltage controlled oscillation unit 23 and the delay unit 50.

The voltage controlled oscillation unit 23 (i.e., a voltage controlled oscillator) generates and outputs an oscillation signal having a frequency based on the output voltage from the loop filter 22 (that is, based on the filtered deviation signal). A voltage controlled oscillator such as a Colpitts VCO (voltage controlled oscillator), a voltage controlled quartz oscillator, or the like can be used as the voltage controlled oscillation unit 23, for example. Note that the above-described voltage controlled oscillation unit 23 may be realized through digital signal processing. The voltage controlled oscillation unit 23 may be configured to be used in combination with a frequency divider. Note that the voltage controlled oscillation unit 23 is connected to the phase/frequency comparison unit 21, and the oscillation signal generated by the voltage controlled oscillation unit 23 is outputted to the phase/frequency comparison unit 21.

On the other hand, as described above, the output signal (output voltage) from the loop filter 22 is also outputted to the delay unit 50, which is provided between the loop filter 22 and the variable low pass filter 60. The delay unit 50 delays the deviation signal that has passed through the loop filter 22 in accordance with an analysis time required by the SN analyzing unit 31 and the phase/frequency analyzing unit 32 (in other words, a delay time), which will be mentioned later, and outputs the delayed signal to the variable low pass filter 60.

The variable low pass filter 60 is capable of changing a cutoff frequency to selectively stop the throughput of a signal and selectively block only a signal in a predetermined frequency band contained in the deviation signal that has been filtered by the loop filter 22. As described below, the variable low pass filter 60 is configured so that the cutoff frequency (a constant) thereof can be controlled and changed by the parameter control unit 40.

A first-order IIR filter or the like that includes one adder, one delay element, and two multipliers, such as that illustrated in FIG. 2, for example, can be used as the variable low pass filter 60. In this case, the cutoff frequency is changed by changing parameters (filter coefficients) of the multipliers. This will be described in detail later. The variable low pass filter 60 is connected to the biological information obtainment unit 70, and the output signal (output voltage) from the variable low pass filter 60 is outputted to the biological information obtainment unit 70.

The biological signal analyzing unit 30 analyzes the approximate frequency, phase, and SN ratio of the photoplethysmographic signal based on the photoplethysmographic signal inputted from the photoplethysmographic sensor 10 and the output of the phase/frequency comparison unit 21. To that end, the biological signal analyzing unit 30 includes the SN analyzing unit 31, which estimates the SN ratio of the photoplethysmographic signal through an autocorrelation analysis on the photoplethysmographic signal, and the phase/frequency analyzing unit (also called "PF analyzing unit" hereinafter) 32, which analyzes the phase difference/frequency difference between the photoplethysmographic signal and the oscillation signal based on the output of the phase/frequency comparison unit 21.

The SN analyzing unit 31 estimates the SN ratio of the photoplethysmographic signal through an autocorrelation analysis on the inputted photoplethysmographic signal. Specifically, the photoplethysmographic signal is normally a periodic signal in which the same pattern repeats every set interval, and thus by normalizing a coefficient $r_k$ obtained through the autocorrelation function indicated in the following Formula (1) with $r_0$ and finding an integrated value thereof, the SN analyzing unit 31 analyzes the periodicity of the photoplethysmographic signal, whether or not artifacts are superimposed, and so on. Note that $\mu$ in Formula (1) represents an average value of a photoplethysmographic signal x, and N represents the number of data in a range subject to the autocorrelation analysis.

Formula 1:
$$r_k = \frac{1}{N}\sum_{n=0}^{N-1}(x[n]-\mu)\cdot(x[n+k]-\mu)(k=0,1,\ldots,N-1) \quad (1)$$

The PF analyzing unit 32 includes a fixed-constant reference low pass filter (LPF), and carries out its analysis by monitoring an output value (an amplitude value) of the reference LPF and changes therein (a differential value). Here, in the case where the PLL unit 20 is synchronized with the photoplethysmographic signal, the output signal of the phase/frequency comparison unit 21 settles near 0 (V), and thus an absolute value of the amplitude value of the reference LPF decreases. Conversely, in the case where the PLL unit 20 is not synchronized with the photoplethysmographic signal, the output of the phase/frequency comparison unit 21 works toward the synchronization of the PLL unit 20, and thus the absolute value of the amplitude of the reference LPF increases. Accordingly, in the case where the output value (amplitude value) of the reference LPF and a change in that output value are lower than a predetermined threshold value, the PF analyzing unit 32 determines that the PLL unit 20 is in synchronization with the input signal (the photoplethysmographic signal). Note that a signal based on a result of the analysis performed by the biological signal analyzing unit 30 (the SN analyzing unit 31 and the PF analyzing unit 32) is outputted to the parameter control unit 40.

The parameter control unit 40 adjusts the cutoff frequency by changing a filter coefficient a (see FIG. 2) of the variable low pass filter 60 based on an analysis result from the biological signal analyzing unit 30, or in other words, based on the SN ratio estimated by the SN analyzing unit 31 and the phase difference/frequency difference between the photoplethysmographic signal and the oscillation signal analyzed by the PF analyzing unit 32.

Specifically, the parameter control unit 40 determines that artifacts are superimposed on the photoplethysmographic signal in the case where the SN ratio is lower than a predetermined value, and sets the filter coefficient a (0.0034, for example) so that the cutoff frequency of the variable low pass filter 60 is a lower value (0.033 Hz, for example) than when the SN ratio is greater than or equal to the predetermined value.

At this time, the parameter control unit 40 sets the filter coefficient a so that the cutoff frequency of the variable low pass filter 60 is lower the lower the SN ratio becomes. To be more specific, the present embodiment is configured such that the cutoff frequency is dynamically controlled by employing the aforementioned first-order IIR filter (see FIG. 2) to determine the value of the filter coefficient a according to the following Formula (2). Note that w in Formula (2) represents a coefficient, outputted from the SN analyzing unit 31, whose value is normalized from 0.0 to 1.0, and is a value that is higher the higher the SN ratio becomes. Meanwhile, the function $f_{NL}$ indicated in Formula (2) is a nonlinear function that takes the coefficient w as an argument, and is expressed, for example, as an exponential function such as that indicated in the following Formula (3); the function is used to emphasize the value of w (note that c=approximately 20.0 in the present embodiment). Finally, the coefficient b is a coefficient that determines the cutoff frequency of the first-order IIR filter indicated in FIG. 2.

Formula 2:

$$a = b \cdot f_{NL}(w) \quad (2)$$

Formula 3:

$$f_{NL}(w) = (c^w - 1)/(c - 1) \ (c > 1.0) \quad (3)$$

By constructing a variable IIR filter in this manner, the cutoff frequency decreases as the SN ratio of the photoplethysmographic signal decreases, and the cutoff frequency can be controlled in accordance with a state of artifacts in the inputted photoplethysmographic signal.

On the other hand, in the case where the SN ratio is greater than or equal to the stated predetermined value and the phase difference/frequency difference is greater than or equal to the stated predetermined threshold value despite it being determined that there are no artifacts superimposed, the parameter control unit 40 determines that the PLL is not in synchronization with the photoplethysmographic signal on which no artifacts are superimposed, and sets the filter coefficient a (0.0342, for example) so that the cutoff frequency of the variable low pass filter 60 is higher (0.333 Hz, for example), than when the SN ratio is lower than the predetermined value and/or the phase difference/frequency difference is lower than the predetermined threshold value (so that the tracking properties are improved).

It is preferable that the stated predetermined value and the stated threshold value used in switching the filter coefficient a prevent erroneous operations (hunting) at the time of the switch by being provided with appropriate hysteresis characteristics.

As described above, the signal filtered by the variable low pass filter 60 is inputted into the biological information obtainment unit 70. The biological information obtainment unit 70 obtains the biological information such as a pulse rate, a pulse beat interval, or the like based on the output signal from the variable low pass filter 60. Note that the obtained biological information such as a pulse rate is outputted to the exterior or stored in the aforementioned RAM or the like.

Figure 3:
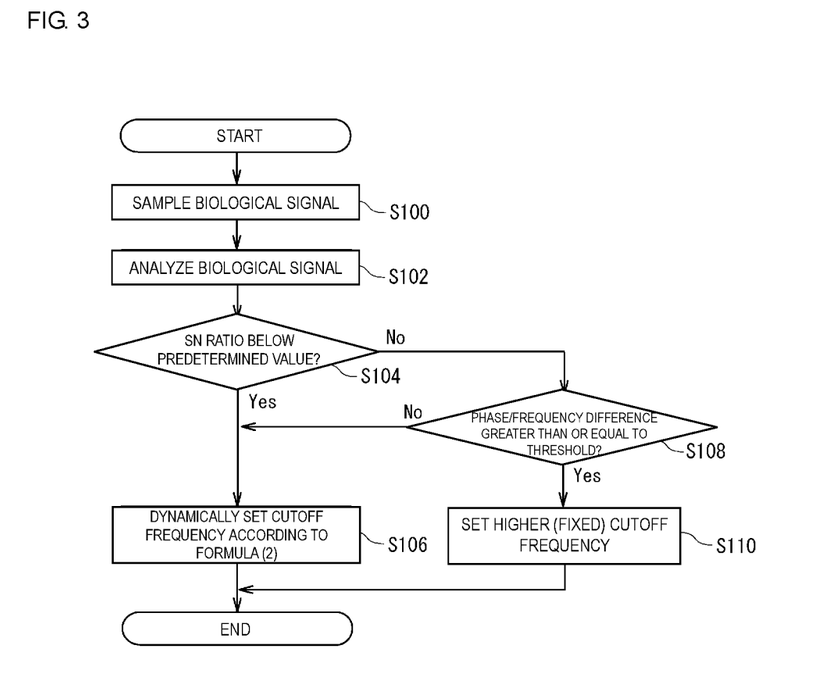
FIG. 3 is a flowchart illustrating the sequence of a biological information measurement process carried out by the biological information measurement apparatus according to the first embodiment.

Next, operations of the biological information measurement apparatus 1 will be described with reference to FIG. 3. FIG. 3 is a flowchart illustrating the sequence of a biological information measurement process carried out by the biological information measurement apparatus 1. The processes indicated in FIG. 3 are repeatedly executed at a predetermined timing (a sampling period), primarily by the signal processing unit 5.

In step S100, the biological signal (photoplethysmographic signal) is sampled. Next, in step S102, the photoplethysmographic signal sampled in step S100 is analyzed by the SN analyzing unit 31 and the PF analyzing unit 32. The details of the analysis performed by the SN analyzing unit 31 and the PF analyzing unit 32 (the SN ratio and the phase/frequency differences) are as described above and thus detailed descriptions thereof will be omitted here.

Next, in step S104, it is determined whether or not the analysis result from the SN analyzing unit 31 (the SN ratio) is less than a predetermined value. In the case where the SN ratio is less than the stated predetermined value (that is, in the case where there are many artifacts), the process moves to step S106. On the other hand, when the SN ratio is greater than or equal to the stated predetermined value (that is, when there are few artifacts), the process moves to step S108.

In step S106, the cutoff frequency of the variable low pass filter 60 is adjusted, in accordance with the stated Formula (2), so as to decrease in accordance with the SN ratio. The process then exits this sequence at a certain period of time.

On the other hand, when it is determined that artifacts are not superimposed, in step S108, it is determined, based on the analysis result from the PF analyzing unit 32, whether or not the phase difference/frequency difference between the photoplethysmographic signal and the oscillation signal of the voltage controlled oscillation unit 23 is greater than or equal to a predetermined threshold value. The process moves to step S110 in the case where the phase difference/frequency difference is greater than or equal to the predetermined threshold value. On the other hand, the process moves to the aforementioned step S106 when the phase difference/frequency difference is less than the predetermined threshold value. Note that the details of the processing performed in step S106 are as described above, and thus detailed descriptions thereof will be omitted here.

In step S110, it is determined that the PLL is not in a synchronized state, and the cutoff frequency of the variable low pass filter 60 is set to a following mode (that is, a mode in which the cutoff frequency is higher so that the input signal can be followed quickly). The process then exits this sequence at a certain period of time.

In this manner, the cutoff frequency (constant) of the variable low pass filter 60 is dynamically controlled by the parameter control unit 40 based on the analysis result from the SN analyzing unit 31 (the SN ratio) and the analysis result from the PF analyzing unit 32 (the phase difference/frequency difference), which constitute the biological signal analyzing unit 30.

Figure 4:
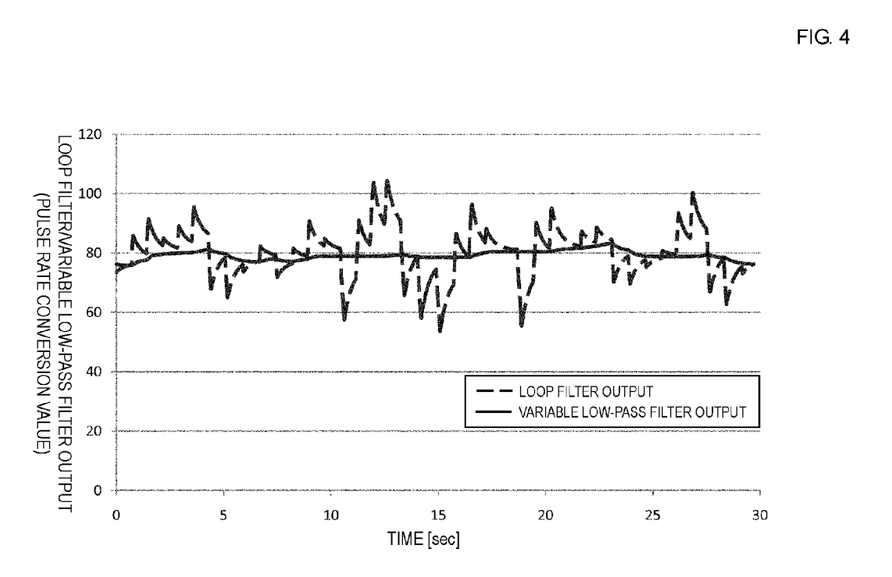
FIG. 4 is a diagram illustrating a body movement noise reduction result achieved by the biological information measurement apparatus according to the first embodiment.

Next, an artifact reduction result achieved by the biological information measurement apparatus 1 will be described in terms of simulation results, using FIG. 4. FIG. 4 is a graph illustrating a difference between an output waveform from the loop filter 22 and an output waveform from the variable low pass filter 60, or in other words, between an output waveform before and after the signal has passed through the variable low pass filter 60. FIG. 4 indicates output waveforms from the loop filter 22 and the variable low pass filter 60, respectively, assuming the pulse rate of the input biological signal (photoplethysmographic signal) is 80 (bpm) and body movement artifacts are superimposed thereon. In FIG. 4, the horizontal axis represents time (sec), and the vertical axis represents the respective outputs (pulse rate conversion values) from the loop filter 22 and the variable low pass filter 60. Furthermore, in FIG. 4, the output (pulse rate conversion value) from the loop filter 22 is represented by a broken line, and the output (pulse rate conversion value) of the variable low pass filter 60 is represented by a solid line.

As illustrated in FIG. 4, the output waveform from the variable low pass filter 60 (the solid line) was confirmed to indicate a successful reduction in the influence of artifacts compared to the output waveform of the loop filter 22 before passing through the variable low pass filter 60 (the broken line). In other words, it was confirmed that the influence of artifacts can be reduced by providing the variable low pass filter 60.

As described thus far, according to the present embodiment, the cutoff frequency of the variable low pass filter 60 is dynamically changed in response to the analysis result from the SN analyzing unit 31 (the SN ratio) and the analysis result from the phase/frequency analyzing unit 32 (the phase difference/frequency difference). Accordingly, the cutoff frequency can be adjusted more appropriately in accordance with fluctuations in the frequency of the inputted biological signal (photoplethysmographic signal), the state of artifacts, and so on. As such, an output signal (frequency synchronization signal) capable of responding to fluctuations in the base frequency of the photoplethysmographic signal and in which artifacts are suppressed can be obtained.

According to the present embodiment, the cutoff frequency of the variable low pass filter 60 is reduced in the case where the SN ratio of the photoplethysmographic signal is lower than a predetermined value, or in other words, in the case where artifacts are superimposed on the photoplethysmographic signal. Accordingly, an output signal in which the influence of artifacts is appropriately suppressed can be obtained.

In addition, according to the present embodiment, the cutoff frequency of the variable low pass filter 60 is reduced as the SN ratio decreases, or in other words, as more artifacts are superimposed, and thus the cutoff frequency can be adjusted more appropriately in accordance with the extent of the artifacts.

On the other hand, according to the present embodiment, the cutoff frequency of the variable low pass filter 60 is increased in the case where the SN ratio is greater than or equal to the predetermined value and the phase difference/frequency difference is greater than or equal to the predetermined threshold value, or in other words, in the case where artifacts are not superimposed but the PLL is not synchronized. Accordingly, the tracking properties with respect to fluctuations in the base frequency can be improved.

Furthermore, the present embodiment is configured including, between the loop filter 22 and the variable low pass filter 60, the delay unit 50 that delays the deviation signal passing through the loop filter 22 and outputs the delayed signal to the variable low pass filter 60 in accordance with the analysis time required by the SN analyzing unit 31 and the phase/frequency analyzing unit 32 (in other words, the delay time). It is thus possible to appropriately compensate for the amount of time required for the SN analyzing unit 31 and the phase/frequency analyzing unit 32 to perform analyses (that is, the delay time).

Second Embodiment

The biological information measurement apparatus 1 according to the above-described first embodiment is configured so that the biological signal analyzing unit 30 includes the SN analyzing unit 31 and the PF analyzing unit 32, and estimates the SN ratio of the photoplethysmographic signal by carrying out an autocorrelation analysis on the photoplethysmographic signal (the biological signal), and analyzes the phase difference/frequency difference between the photoplethysmographic signal and the oscillation signal with respect to the output of the phase/frequency comparison unit 21. However, the configuration may be such that the frequency analysis is carried out by executing an orthogonal transform such as an FFT on the photoplethysmographic signal and detecting a state of the photoplethysmographic signal, such as the approximate frequency, phase, noise level, and the like of the photoplethysmographic signal, for example.

Figure 5:
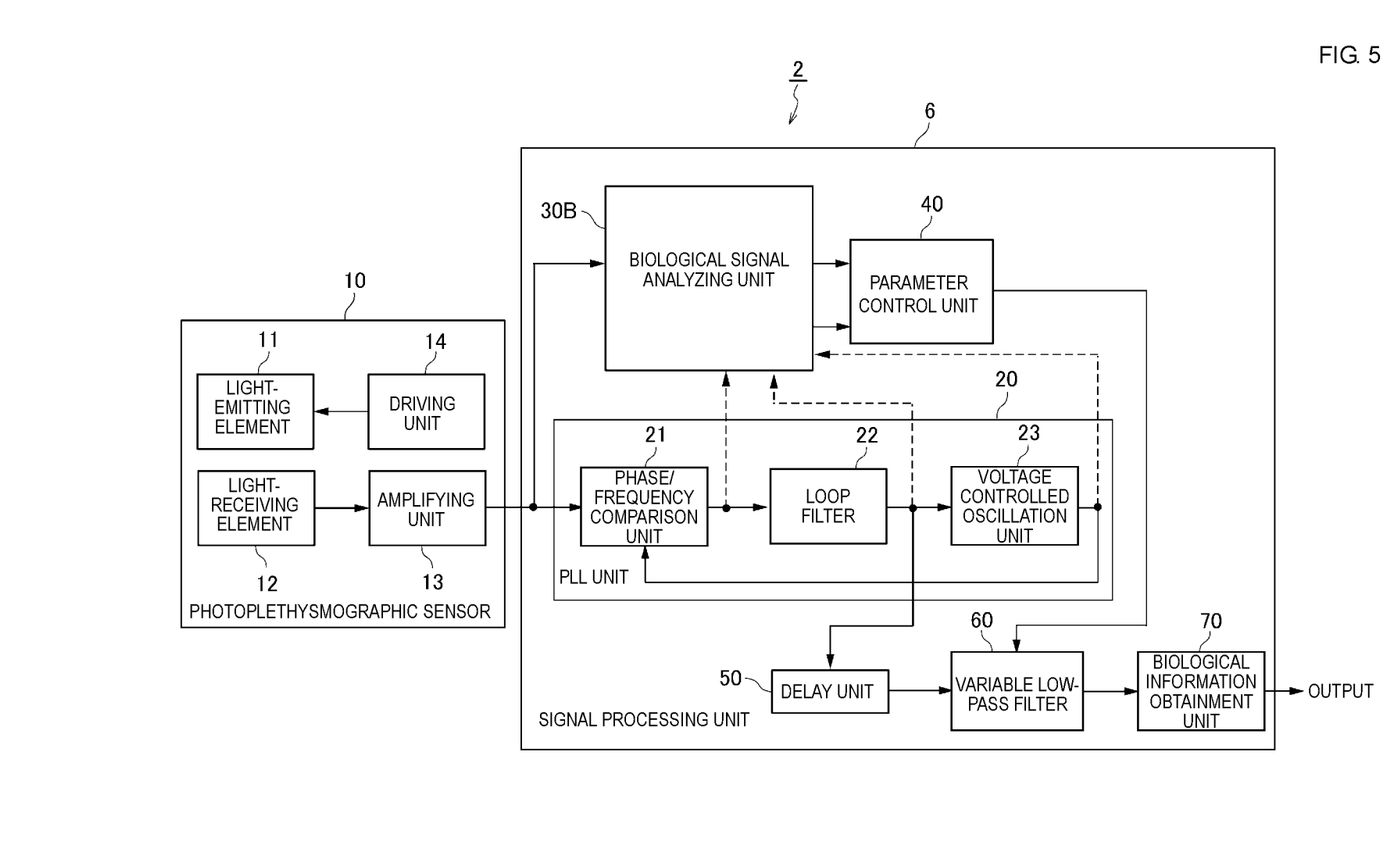
FIG. 5 is a block diagram illustrating the configuration of a biological information measurement apparatus according to a second embodiment.

Accordingly, next, the configuration of a biological information measurement apparatus 2 according to a second embodiment will be described using FIG. 5. Here, descriptions of configurations that are identical or similar to those in the biological information measurement apparatus 1 according to the above-described first embodiment will be simplified or omitted, and primarily the points of difference will be described. FIG. 5 is a block diagram illustrating the configuration of the biological information measurement apparatus 2. In FIG. 5, constituent elements that are the same or equivalent to those in the first embodiment have been given the same reference numerals.

The biological information measurement apparatus 2 differs from the biological information measurement apparatus 1 in that a biological signal analyzing unit 30B is provided instead of the biological signal analyzing unit 30 that includes the SN analyzing unit 31 and the PF analyzing unit 32. The other configurations are the same or similar to those in the aforementioned biological information measurement apparatus 1, and thus detailed descriptions thereof will be omitted.

The biological signal analyzing unit 30B obtains an approximate frequency, phase, and SN ratio (a noise state) of an inputted photoplethysmographic signal by analyzing the photoplethysmographic signal. To be more specific, by carrying out an orthogonal transform such as a FFT on the photoplethysmographic signal, the biological signal analyzing unit 30B obtains the approximate frequency of the photoplethysmographic signal, determines a frequency component that differs from that frequency component (the frequency component of a photoplethysmograph being 0.666-6.666 Hz, for example) to be noise, and finds a level and the like of that noise.

It should be noted that according to the biological signal analyzing unit 30B, the state of the photoplethysmographic signal may be analyzed based on one or more of the output signal of the phase/frequency comparison unit 21, the output signal of the loop filter 22, and the output signal of the voltage controlled oscillation unit 23, instead of or in addition to the inputted photoplethysmographic signal.

As in the above-described first embodiment, the parameter control unit 40 dynamically changes the cutoff frequency (constant) of the variable low pass filter 60 based on the analysis results from the biological signal analyzing unit 30B, or in other words, based on the approximate frequency, phase, and SN ratio (noise state) of the photoplethysmographic signal.

Note that the biological signal analyzing unit 30B may determine the state of the photoplethysmographic signal by carrying out a time-series analysis on the photoplethysmographic signal. In this case, the state of the photoplethysmographic signal is determined by carrying out a time-series analysis for detecting a seasonal component (pulse beat component) contained in the photoplethysmographic signal and a noise component caused by artifacts.

According to the present embodiment, the approximate frequency, phase, and SN ratio of the photoplethysmographic signal are analyzed, and the cutoff frequency of the variable low pass filter 60 is dynamically changed based on the result of that analysis. Accordingly, the cutoff frequency of the variable low pass filter 60 can be adjusted dynamically in accordance with fluctuations in the frequency of the inputted biological signal (photoplethysmographic signal), the state of artifacts, and so on. As such, an output signal (frequency synchronization signal) capable of responding to fluctuations in the base frequency of the photoplethysmographic signal and in which artifacts are suppressed can be obtained.

In particular, according to the present embodiment, the phase, frequency, SN ratio of the photoplethysmographic signal are analyzed by carrying out an orthogonal transform (FFT) on the photoplethysmographic signal. As such, the approximate frequency, phase, and SN ratio of the photoplethysmographic signal, in which the pulse rate varies over time and on which artifacts produced by body movements and the like are superimposed, can be analyzed appropriately.

Although embodiments of the present invention have been described thus far, the present invention is not intended to be limited to the aforementioned embodiments, and many variations can be carried out thereon. For example, although the above embodiments describe configurations in which biological information such as a pulse rate is measured by detecting a photoplethysmographic signal (a biological signal) using the photoplethysmographic sensor 10, the configuration may be such that biological information such as a pulse rate is measured by detecting an electrocardiac signal (biological signal) using an electrocardiac sensor, for example, instead of or in addition to the photoplethysmographic sensor 10.

In addition, although the variable low pass filter 60 is connected to the loop filter 22 in the above-described embodiments, the configuration may be such that the variable low pass filter 60 is connected to the voltage controlled oscillation unit 23. In this case, the output of the voltage controlled oscillation unit 23 is inputted into the variable low pass filter 60 after undergoing a process for being converting into a pulse rate. To be more specific, the pulse rate is found by detecting a peak or a zero cross point from the output of the voltage controlled oscillation unit 23, and is then inputted into the variable low pass filter 60 after undergoing an interpolation process for setting a sampling period of the obtained pulse rate to a constant period.

Furthermore, although in the above-described embodiment, the cutoff frequency is set by determining the value of the filter coefficient a of the first-order IIR filter through Formula (2) when reducing the cutoff frequency of the variable low pass filter 60 as the SN ratio decreases, the method for setting the cutoff frequency is not limited to the above-described embodiments.

REFERENCE SIGNS LIST 1, 2 BIOLOGICAL INFORMATION MEASUREMENT APPARATUS
5, 6 SIGNAL PROCESSING UNIT
10 PHOTOPLETHYSMOGRAPHIC SENSOR
20 PLL UNIT
21 PHASE/FREQUENCY COMPARISON UNIT
22 LOOP FILTER
23 VOLTAGE CONTROLLED OSCILLATION UNIT
30, 30B BIOLOGICAL SIGNAL ANALYZING UNIT
31 SN ANALYZING UNIT
32 PHASE/FREQUENCY ANALYZING UNIT
40 PARAMETER CONTROL UNIT
50 DELAY UNIT
60 VARIABLE LOW PASS FILTER
70 BIOLOGICAL INFORMATION OBTAINMENT UNIT

The invention claimed is:

1. A biological information measurement apparatus comprising:
   a sensor configured to detect a biological signal;
   a phase/frequency comparator configured to output a deviation signal based on a phase difference/frequency difference between the biological signal and an oscillation signal;
   a loop filter configured to block a signal of a predetermined frequency band contained in the deviation signal;
   a voltage controlled oscillator coupled to the phase/frequency comparator and configured to generate the oscillation signal based on the deviation signal that has been filtered by the loop filter;
   a low pass filter coupled to an output of the loop filter, the low pass filter having a variable cutoff frequency to selectively block a signal of a predetermined frequency band contained in the deviation signal that has been filtered by the loop filter; and
   a computer processing unit configured to analyze a phase, a frequency, and a SN ratio of the biological signal and change the variable cutoff frequency of the low pass filter based on the analyzed phase, frequency and SN ratio of the biological signal.

2. The biological information measurement apparatus according to claim 1, wherein the computer processing unit is further configured to analyze the phase, the frequency, and the SN ratio of the biological signal by an orthogonal transformation of the biological signal.

3. The biological information measurement apparatus according to claim 1, wherein the computer processing unit is further configured to:
   estimate the SN ratio of the biological signal based on an autocorrelation of the biological signal,
   analyze the phase difference/frequency difference between the biological signal and the oscillation signal based on the deviation signal output by the phase/frequency comparator, and
   change the variable cutoff frequency of the low pass filter based on the estimated SN ratio and the analyzed phase difference/frequency difference between the biological signal and the oscillation signal.

4. The biological information measurement apparatus according to claim 3, wherein the computer processing unit is configured to reduce the variable cutoff frequency of the low pass filter more when the SN ratio is lower than a predetermined value than when the SN ratio is greater than or equal to the predetermined value.

5. The biological information measurement apparatus according to claim 4, wherein the computer processing unit is further configured to further reduce the variable cutoff frequency of the low pass filter unit as the SN ratio of the biological signal decreases.

6. The biological information measurement apparatus according to claim 4, wherein the computer processing unit is further configured to increase the variable cutoff frequency of the low pass filter unit more when the SN ratio is greater than or equal to the predetermined value and the phase difference/frequency difference is greater than or equal to a predetermined threshold value than when at least one of the SN ratio is lower than the predetermined value and the phase difference/frequency difference is lower than the predetermined threshold value.

7. The biological information measurement apparatus according to claim 1, further comprising a delay unit disposed between the loop filter and the low pass filter and configured to delay the deviation signal that has been filtered by the loop filter.

8. The biological information measurement apparatus according to claim 7, wherein the delay unit is configured to delay the deviation signal for a time period based on an analysis time required by the computer processing unit to analyze a phase, a frequency, and a SN ratio of the biological signal.

9. The biological information measurement apparatus according to claim 3, further comprising a delay unit disposed between the loop filter and the low pass filter and configured to delay the deviation signal that has been filtered by the loop filter.

10. The biological information measurement apparatus according to claim 9, wherein the delay unit is configured to delay the deviation signal for a time period based on an analysis time required by the computer processing unit to analyze a phase, a frequency, and a SN ratio of the biological signal and to analyze the phase difference/frequency difference between the biological signal and the oscillation signal.

11. The biological information measurement apparatus according to claim 1, wherein the low pass filter comprises a first-order infinite impulse response filter including an adder, a delay element, and pair of multipliers.

12. The biological information measurement apparatus according to claim 11, wherein the computer processing unit is configured to change the variable cutoff frequency of the low pass filter by changing at least one filter coefficient of at least one of the pair of multipliers.

13. The biological information measurement apparatus according to claim 1, wherein the sensor includes:
 a light-emitting element that emits light based on a pulse-form driving signal;
 a light-receiving element that outputs a detection signal based on an intensity of incident light that has been emitted from the light-emitting element and passed through a human body or reflected by the human body; and
 an amplifying unit that amplifies the detection signal as the biological signal.

14. A method for measuring biological information, the method comprising:
 detecting, by a sensor, a biological signal;
 generating a deviation signal by comparing a phase difference/frequency difference between the biological signal and an oscillation signal;
 blocking, by a loop filter, a signal of a predetermined frequency band contained in the deviation signal;
 generating, by a voltage controlled oscillator, the oscillation signal based on the deviation signal that has been filtered by the loop filter;
 selectively blocking, by a low pass filter having a variable cutoff frequency, a signal of a predetermined frequency band contained in the deviation signal that has been filtered by the loop filter;
 analyzing, by a computer processing unit, a phase, a frequency, and a SN ratio of the biological signal; and
 changing, by a computer processing unit, the variable cutoff frequency of the low pass filter based on the analyzed phase, frequency and SN ratio of the biological signal.

15. The method according to claim 14, further comprising analyzing, by the computer processing unit, the phase, the frequency, and the SN ratio of the biological signal by an orthogonal transformation of the biological signal.

16. The method apparatus according to claim 14, further comprising:
 estimating, by the computer processing unit, the SN ratio of the biological signal based on an autocorrelation of the biological signal;
 analyzing, by the computer processing unit, the phase difference/frequency difference between the biological signal and the oscillation signal based on the deviation signal output by the phase/frequency comparator; and
 changing, by the computer processing unit, the variable cutoff frequency of the low pass filter based on the estimated SN ratio and the analyzed phase difference/frequency difference between the biological signal and the oscillation signal.

17. The method according to claim 16, further comprising reducing, by the computer processing unit, the variable cutoff frequency of the low pass filter more when the SN ratio is lower than a predetermined value than when the SN ratio is greater than or equal to the predetermined value.

18. The method according to claim 17, further comprising further reducing, by the computer processing unit, the variable cutoff frequency of the low pass filter unit as the SN ratio of the biological signal decreases.

19. The method according to claim 17, further comprising increasing, by the computer processing unit, the variable cutoff frequency of the low pass filter unit more when the SN ratio is greater than or equal to the predetermined value and the phase difference/frequency difference is greater than or equal to a predetermined threshold value than when at least one of the SN ratio is lower than the predetermined value and the phase difference/frequency difference is lower than the predetermined threshold value.

20. The method according to claim 14, further comprising delaying, by a delay unit disposed between the loop filter and the low pass filter, the deviation signal that has been filtered by the loop filter for a time period based on an analysis time required by the computer processing unit to analyze a phase, a frequency, and a SN ratio of the biological signal.

* * * * *